United States Patent [19]

Ballard et al.

[11] Patent Number: 5,744,730
[45] Date of Patent: Apr. 28, 1998

[54] SUBSURFACE IN-SITU RADON GAS DETECTION/PENETROMETER SYSTEM

[76] Inventors: John H. Ballard, 106 Pinehaven Cove, Clinton, Miss. 39056-3123; John C. Morgan, 211 Bellbottom Rd., Redwood, Miss. 39058

[21] Appl. No.: 800,490

[22] Filed: Feb. 14, 1997

[51] Int. Cl.⁶ .................. G01N 1/26; E21B 49/00
[52] U.S. Cl. ................... 73/864.74; 73/864.63; 175/50; 175/59
[58] Field of Search ............ 73/864.43, 864.44, 73/864.45, 864.63, 864.74, 864.84; 175/50, 58, 59, 21; 250/254, 255

[56] References Cited

U.S. PATENT DOCUMENTS

| | | | |
|---|---|---|---|
| 2,376,366 | 5/1945 | Lawlor et al. | 73/864.63 |
| 3,611,799 | 10/1971 | Davis | 175/50 |
| 4,804,050 | 2/1989 | Kerfoot | 73/864.74 |
| 4,807,707 | 2/1989 | Handley et al. | 73/864.74 |
| 4,814,608 | 3/1989 | Dempsey et al. | 250/255 |
| 5,150,622 | 9/1992 | Vollweiler | 73/864.74 |
| 5,179,285 | 1/1993 | Langner, Jr. | 250/253 |
| 5,358,057 | 10/1994 | Peters et al. | 73/864.74 |
| 5,421,419 | 6/1995 | Heller et al. | 175/59 |
| 5,435,176 | 7/1995 | Manchak, III | 175/50 |
| 5,489,780 | 2/1996 | Diamondis | 250/370.02 |

Primary Examiner—Ronald L. Biegel
Attorney, Agent, or Firm—Luther A. Marsh

[57] ABSTRACT

A penetrometer probe for detecting the presence of subsurface radon gas and obtaining soil classification data is characterized by an elongated body containing recessed inlet and outlet ports, a sampling chamber, a vacuum/air controlled valve system having pistons displaceable between open and closed positions, and a vacuum/air system for drawing gas samples into and expelling gas samples from the sampling chamber. The probe also includes a detachable tip which allows grout to be injected into the borehole as the probe is withdrawn. In an alternate embodiment, the probe includes an outer sleeve for controlling the taking of gas samples in which the sleeve slides upwardly in a groove contained in the probe body during penetration, thereby covering the gas sampling ports, and slides downwardly during retraction, thereby uncovering the soil gas sampling ports and allowing gas to flow to the sampling chamber.

13 Claims, 2 Drawing Sheets

SUBSURFACE IN-SITU RADON GAS DETECTION/PENETROMETER SYSTEM

BACKGROUND OF THE INVENTION

The present invention relates to gas detecting penetrometers and, more particularly, to a penetrometer for detecting the presence of a radioactive gas, such as radon, in real time at multiple locations in a penetrometer borehole without bringing a sample to the surface. The penetrometer is capable of sealing the borehole by filling it with grout while being withdrawn therefrom.

BRIEF DESCRIPTION OF THE PRIOR ART

Radon gas is a known health hazard found to naturally occur in some soils and which collects in basements and other structures. To minimize the risks associated with radon gas, there is an ongoing need to safely and accurately detect the subsurface presence of the gas.

One method currently used for detecting the presence of radon gas or, more accurately, the alpha particles of radon gas, includes sampling soil for alpha emitting radiation. This method, however, is time consuming, costly, and requires bringing soil samples to a laboratory for analysis. Radon gas may also be detected by collecting air samples from suspect locations and sending the samples to a laboratory for analysis. In some instances, boreholes may be used to collect subsurface gas samples for later laboratory analysis. Various devices are known in the patented prior art for extracting gas samples from the ground as shown, for example, in the U.S. patents to Brame U.S. Pat. No. 4,310,057, Bartz U.S. Pat. No. 4,335,622, Richers U.S. Pat. No. 4,452,091, and Vollweiler U.S. Pat. No. 5,150,622. These devices serve only to extract gas samples from the ground and do not detect the presence of gas. In addition, the use of these devices is imprecise since the origin of the gas is unknown and may have emanated From any depth or soil layer within the borehole.

The U.S. patent to Handley et al U.S. Pat. No. 4,807,707 discloses a sampling system for obtaining subsurface samples of soil gas and ground water. The system includes a sampling probe having a housing and a telescoping head and includes a computer monitoring system for collecting the desired amount of sample, storing data for later analysis, and monitoring conditions in the probe housing such as gas pressure and water level. An umbilical tube provides pressurized gas to the probe housing to extend the head therefrom. Upon depressurization, ground water or gases flow through a check valve into the probe housing. The patent also discloses withdrawing samples through the umbilical tube by applying a negative pressure from a vacuum system to the umbilical tube.

The U.S. patent to Peters et al U.S. Pat. No. 5,358,057 discloses a penetrometer probe for taking multiple soil-gas and ground water samples. The probe includes a housing containing a sampling cavity, a pressure/vacuum activated piston displaceable between open and closed positions, and sensors for analyzing the sample.

The U.S. patent to Dempsey et al U.S. Pat. No. 4,814,608 discloses a system for measuring a radioactive gas, such as radon, in a subsoil environment. To obtain a measurement, the device is inserted and kept in the soil for a predetermined period of time, then removed and disassembled. This device exposes investigators to potentially harmful contaminants and does not provide continuous or real-time data output.

The present invention was developed in order to overcome these and other drawbacks of the prior devices by providing an earth penetrating probe for detecting hazardous gas below ground. The probe includes an elongated body having inlet and outlet ports for taking and discharging samples, respectively, an alpha particle detector for analyzing the sample, regulating means for controlling the taking of samples, a removable cone tip, and a grouting system that ejects grout into the borehole as the probe is withdrawn from the borehole.

SUMMARY OF THE INVENTION

Accordingly, a primary object of the present invention is to provide a probe for the subsurface detection of hazardous gases, such as radon.

It is a more specific object of the invention to provide a probe having a housing body with a conical end adapted to penetrate the ground, inlet and outlet ports for sampling and discharging samples of the gas, respectively, an alpha particle detector for analyzing samples of gas taken from the borehole, a removable cone tip, and a grouting system that ejects grout from the tip end of the probe into the borehole as the probe is withdrawn from the borehole.

It is another object of the invention to provide a gas detecting probe which can detect the presence of radon gas in real-time without bringing a sample to the surface.

It is a further object of the present invention to provide a gas detecting probe which can detect the presence of radon gas at a plurality of discrete locations in the borehole, thus allowing the precise soil layer which emits radon gas to be identified.

It is yet another object of the present invention to provide a gas detecting probe having on outer sleeve which slides downwardly on the probe body as the probe is moved upwardly in the borehole, thereby uncovering the inlet ports so that soil-gas samples may be obtained.

It is still another object of the invention to provide a gas detecting probe having strain sensors mounted on the outer surface thereof for providing soil classification data.

A still further object of the present invention is to provide a gas detecting probe which can quickly, accurately, and inexpensively detect hazardous gas in soil below ground.

BRIEF DESCRIPTION OF THE DRAWINGS

Other objects and advantages of the invention will become apparent from a study of the following specification when viewed in the light of the accompanying drawings in which.

DETAILED DESCRIPTION

Figure 1:
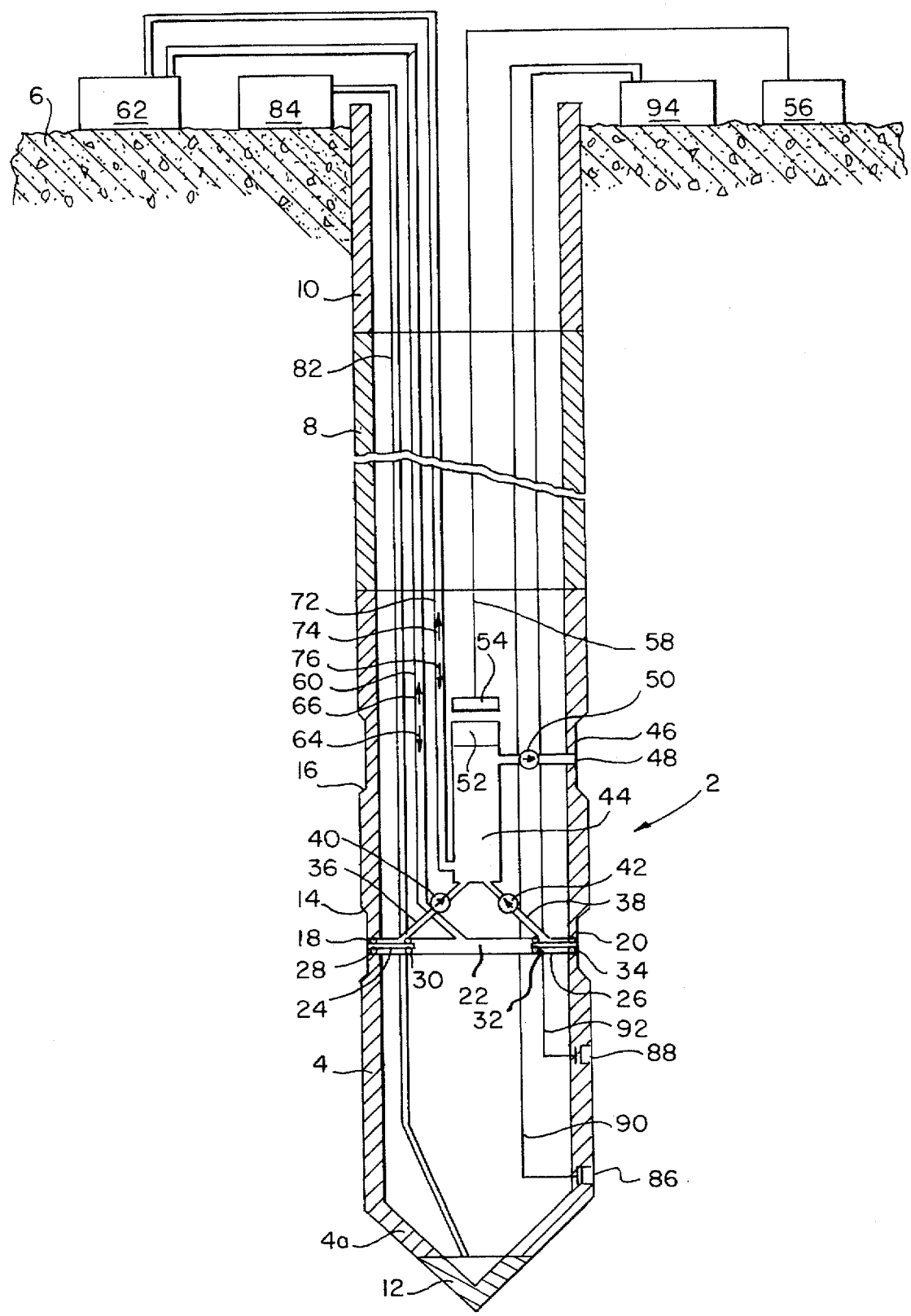
FIG. 1 is a longitudinal sectional view of the gas detecting penetrometer according to the present invention.

Referring first to FIG. 1 there is shown a gas detecting soil classifying penetrometer probe 2 having a vertically arranged elongated body 4 penetrating the ground 6. The longitudinal axis of the probe 2 is arranged generally vertically during penetration. The probe is driven into the ground with hollow push rods 8 and 10 and surface mounted hydraulic equipment (not shown) and forms a borehole as it penetrates the ground.

The probe body 4 includes a conically shaped penetrating end portion 4a and a tip 12 detachably mounted on end portion 4a. The body contains a pair of longitudinally spaced annular grooves or recesses 14 and 16. Groove 14 is laterally spaced below groove 16 and contains a pair of aligned oppositely facing inlet ports 18 and 20 affording communication with a transverse passage 22 arranged therebetween.

A pair of pistons 24 and 26 are movably retained within passage 22, each piston having a pair of O-rings 28, 30 and 32, 34, respectively, mounted thereon. A pair of inlet conduits 36 and 38 are connected at their lower ends with transverse passage 22 and contain check valves 40 and 42, respectively, which allow flow only in the direction indicated by the arrows in the respective valves. The upper ends of conduits 36 and 38 are connected with the bottom of a sampling chamber 44.

An exit or outlet passage 46 is connected with and affords communication between the upper end of sampling chamber 44 and an outlet port 48 contained in groove 16. Passage 46 includes a check valve 50 which allows flow only in the direction of outlet port 48.

An alpha particle detector 52 connected with the top of the sampling chamber 44 analyzes the contents of the sampling chamber 44 to determine if any alpha particles of radon gas are present which, in turn, indicates the presence of radon gas. A pre-amplifier- 54 connected with particle detector 52 amplifies the data signal transmitted by the particle detector and the amplified signal is transmitted to surface mounted data acquisition and processing equipment 56 via transmission line 58.

Figure 2:
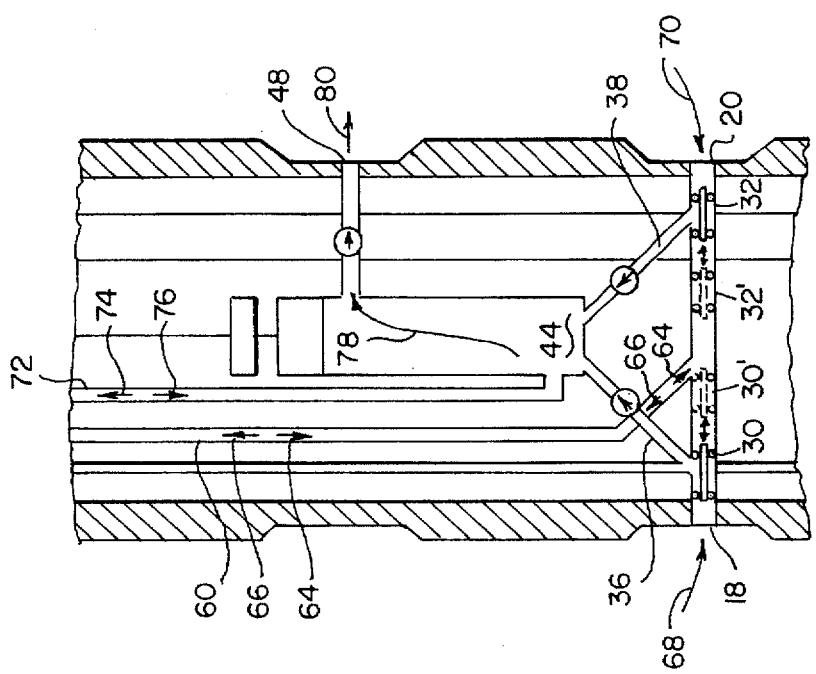
FIG. 2 is a detailed sectional view of the regulating means and sampling chamber of the penetrometer of FIG. 1.

A valve actuating vacuum-air line 60 is connected with a surface mounted vacuum-air controller 62 at one end and at the other end with transverse passage 22 intermediate inlet conduits 36 and 38. Line 60 provides positive air pressure as indicated by arrow 64 or negative air pressure which creates a vacuum as indicated by arrow 66. As shown in FIG. 2, positive air pressure 64 causes pistons 30 and 32 to move outwardly, thereby closing inlet ports 18 and 20, respectively, and preventing soil gas, indicated by arrows 68 and 70, from flowing into sampling chamber 44 via inlet conduits 36 and 38.

When the air flow direction is reversed as shown by arrow 66, a negative air pressure is created, thereby causing pistons 30 and 32 to move inwardly together as shown in phantom 30' and 32'. In this position, ports 18 and 20 are open, thereby allowing gas to flow to the sampling chamber 44 via inlet conduits 36 and 38. Ports 18 and 20 are closed by again reversing the airflow causing the pistons 30 and 32 to move outwardly as described above.

A sample control vacuum-air line 72 is also connected with the vacuum-air controller 62 at its upper end and is connected with the lower end of the sampling chamber 44 at its lower end. Line 72 serves to draw samples into the sampling chamber 44 when the ports 18 and 20 are open by creating a negative or vacuum pressure indicated by arrow 74. Line 72 also serves to purge soil gas samples 78 from the sampling chamber 44 by providing air indicated by arrow 76 to the chamber, whereby the soil gas 78 is expelled from the sampling chamber 44 through outlet port 48 into the subsurface media surrounding the probe. Once the gas is expelled, the penetrometer has the capability of being moved to a different depth for additional sampling.

A grout ejection tube 82 is connected with and extends from a surface mounted grout pumping system-controller 84, through the hollow push rods 8 and 10, and probe body 4, to the probe tip 12. As the probe is inserted into the ground, it forms a borehole within which soil gas measurements are taken. Once the measurements are completed, the probe is retracted or withdrawn from the borehole. To avoid contaminating the surrounding environment, it is desirable to seal the borehole when the probe is withdrawn therefrom. This is accomplished by ejecting tip 12 from the probe, thus allowing grout supplied from controller 84 to be injected into the borehole through tube 82 as the probe is moved upwardly and removed from the borehole. Accordingly, the probe allows in-ground soil gas analysis without bringing radioactive contaminants to the surface and seals the borehole once tests are completed.

Soil classification tip and sleeve strain sensors 86 and 88, respectively, are mounted on the inner surface of the probe body 4 and are connected with transmission wires 90 and 92, respectively, which are connected with a surface mounted soil classification data acquisition-processor system 94, thereby allowing soil classification and layering information to be obtained.

Figure 3:
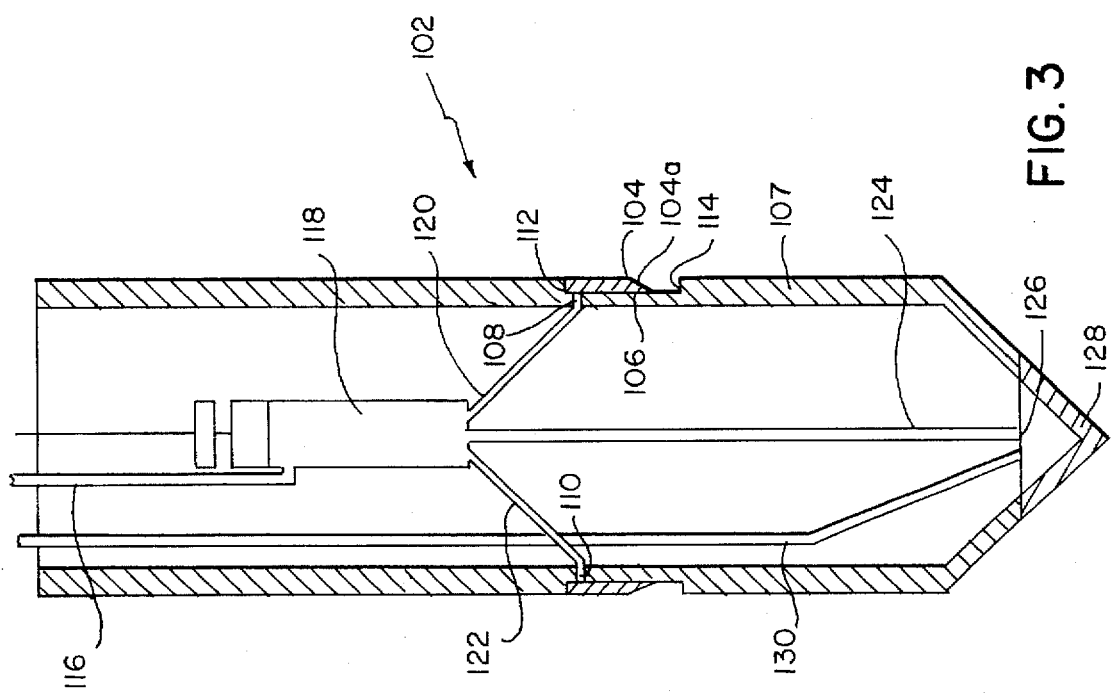
FIG. 3 is a longitudinal sectional view of a second embodiment of the invention.

Referring now to FIG. 3, there is shown a modified probe 102 having an outer sleeve 104 slidably arranged in a peripheral groove 106 contained in the probe body 107. In this embodiment, the piston-valve actuating system for controlling the taking of samples has been replaced with a sleeve 104. A pair of sampling ports 108 and 110 are contained in groove 106 such that when the sleeve is seated against the upper shoulder 112 of groove 106, the sampling ports are covered and no soil-gas can flow to the sampling chamber 118. The covered condition occurs during penetration when friction from the surrounding soil causes the sleeve to slide upwardly over the sampling ports. Conversely, when the probe is moved slightly upwardly in the borehole, friction between the sleeve and surrounding soil causes the sleeve to slide downwardly in groove 106 until it abuts lower shoulder 114, thereby uncovering sampling ports 110 and 112 so that gas samples can be obtained. To facilitate sliding movement of the sleeve in the groove, the lower end of sleeve 104 is tapered 104a to clear debris which may accumulate in groove 106 during penetration.

A vacuum/air line 116 is connected with the upper end of the sampling chamber 118 and serves to draw gas samples through the sampling ports 108 and 110 into the sampling chamber 118 via conduits 120 and 122 when sleeve 104 is seated against shoulder 114 and ports 108 and 110 are uncovered. Line 116 also serves to eject the soil gas sample from the sampling chamber through an outflow gas line 124 which extends from the bottom of the sampling chamber to an outlet port 126 adjacent the probe tip 128.

The remainder of the probe is identical to that of FIG. 1 and while not shown, it will be recognized that the probe of FIG. 3 can also be provided with soil classification strain sensors as described above.

Both embodiments allow investigators to conduct real time data acquisition of both spectral alpha radiation and subsurface soil classification data. In addition, the penetrometers allow analyses to be conducted at multiple vertical locations within the borehole, thereby allowing the specific contaminated soil layers to be identified. Subsurface gas detection is accomplished quickly and accurately without exposing investigators to the contaminants and without bringing samples containing radioactive contaminants to the surface for conventional radiation analysis. In addition, contamination of the surrounding environment is prevented by grouting the borehole as the probe is removed therefrom.

While in accordance with the provisions of the Patent Statutes the preferred forms and embodiments of the invention have been illustrated and described, it will be apparent to those of ordinary skill in the art that various changes and modifications may be made without deviating from the inventive concept set forth above.

What is claimed is:

1. A probe for taking a sample of soil-gas in a borehole and analyzing the soil-gas sample for the presence of a pre-selected gas while in the ground, comprising:
   (a) an elongated body adapted to penetrate the ground, said body having an outer surface containing at least one inlet port and at least one outlet port, said body further containing a sampling chamber in fluid communication with said ports;
   (b) detecting means connected with said sampling chamber for detecting the pre-selected gas; and
   (c) regulating means for selectively allowing the soil-gas sample to flow from said inlet port to said sampling chamber.

2. A probe as defined in claim 1, and further comprising sample control means in fluid communication with said sampling chamber for drawing the soil-gas sample into said sampling chamber and expelling the soil-gas sample from said sampling chamber, thereby allowing soil-gas samples to be analyzed at multiple locations in the borehole.

3. A probe as defined in claim 2, wherein said sample control means includes a surface mounted pressure/vacuum controller connected with said sampling chamber.

4. A probe as defined in claim 3, wherein said body has a longitudinal axis arranged generally vertically during penetration, said body including an ejectable conically shaped tip at its penetrating end.

5. A probe as defined in claim 4, wherein said apparatus includes a grout tube extending from said tip through said body to ground level, whereby grout may be injected into the borehole as said probe is withdrawn therefrom.

6. A probe as defined in claim 5, wherein said body outer surface contains a pair of longitudinally spaced annular grooves containing said inlet and outlet ports, respectively.

7. A probe as defined in claim 6, wherein said detecting means comprises a particle detector and a pre-amplifier.

8. A probe as defined in claim 7, wherein said regulating means comprises a control valve having at least one piston displaceable between a retracted position allowing soil-gas flow to said sampling chamber and an actuated position preventing soil-gas flow to said sampling chamber.

9. A probe as defined in claim 8, wherein said control valve is actuated by said surface mounted pressure/vacuum controller.

10. A probe as defined in claim 9, wherein the soil-gas is expelled from said sampling chamber by said surface mounted pressure/vacuum controller.

11. A probe as defined in claim 10, and further comprising at least one pressure transducer means mounted on said body outer surface for measuring pressure applied to said outer surface.

12. A probe as defined in claim 1, wherein said regulating means comprises an annular sleeve adapted to slide along said body outer surface between a first position covering said at least one inlet port and a second position uncovering said at least one inlet port.

13. A probe as defined in claim 12, wherein said sleeve is actuated from said seated position to said unseated position by moving said body upwardly in the borehole.

* * * * *